(12) United States Patent
Derer

(10) Patent No.: US 10,387,615 B2
(45) Date of Patent: Aug. 20, 2019

(54) ESTIMATE ANALYSIS AND VALIDATION

(71) Applicant: Passport Health Communications, Inc., Franklin, TN (US)

(72) Inventor: Richard Frank Derer, Clarendon Hills, IL (US)

(73) Assignee: PASSPORT HEALTH COMMUNICATIONS, INC, Franklin, TN (US)

( * ) Notice: Subject to any disclaimer, the term of this patent is extended or adjusted under 35 U.S.C. 154(b) by 354 days.

(21) Appl. No.: 14/024,275

(22) Filed: Sep. 11, 2013

(65) Prior Publication Data

US 2014/0095188 A1 Apr. 3, 2014

Related U.S. Application Data

(60) Provisional application No. 61/707,204, filed on Sep. 28, 2012.

(51) Int. Cl.
*G06F 19/00* (2018.01)

(52) U.S. Cl.
CPC .................. *G06F 19/328* (2013.01)

(58) Field of Classification Search
CPC .................................................... G06F 19/328
See application file for complete search history.

(56) References Cited

U.S. PATENT DOCUMENTS

2003/0069760 A1* 4/2003 Gelber ............................ 705/4
2008/0274815 A1* 11/2008 Root ............................ 463/48

* cited by examiner

*Primary Examiner* — Jonathan Durant
*Assistant Examiner* — Gregory D. Moseley
(74) *Attorney, Agent, or Firm* — Merchant & Gould

(57) ABSTRACT

Validating patient payment estimates is provided. Validating patient payment estimates may comprise matching patient payment estimates with claims, payments and insurance contracts and providing tools to analyze the results of the matching process. Discrepancies may be determined, for example discrepancies between procedures and patient portions from the estimate with procedures actually billed and paid and a patient portion determined by the insurance company. Results may be stored in a dashboard user interface, which may then be available via a user interface for drill-down analysis.

18 Claims, 4 Drawing Sheets

ESTIMATE ANALYSIS AND VALIDATION

CROSS-REFERENCE TO RELATED APPLICATIONS

The application claims priority to U.S. Provisional Patent Application No. 61/707,204 titled "Estimate Analysis and Validation" filed Sep. 28, 2012, the disclosure of which is hereby incorporated by reference in its entirety.

BACKGROUND

When a patient seeks healthcare services from a healthcare provider, an estimate of the patient's financial responsibility for the services may be provided to the patient or to a guarantor for the patient's account. The estimate may be calculated according to various factors including a selection of procedures that may be performed.

To help with accuracy of estimates and for quality assurance purposes, estimates may be tested for accuracy. Currently when testing an estimate for accuracy, the estimate may be analyzed manually against claims and payments related to the estimate. As can be appreciated, this may be a time-consuming process and may be prone to human error.

It is with respect to these and other considerations that the present invention has been made.

SUMMARY

Embodiments of the present invention provide for validating patient payment estimates. An automated system is provided for periodically or selectively reviewing and comparing an estimate, a claim that is billed to the estimate, and one or more payments paid on the claim. Metrics may be provided in a dashboard for quantifying a validation or invalidation.

BRIEF DESCRIPTION OF THE DRAWINGS

The accompanying drawings, which are incorporated in and constitute a part of this disclosure, illustrate various embodiments of the present invention. In the drawings.

DETAILED DESCRIPTION

Figure 1:
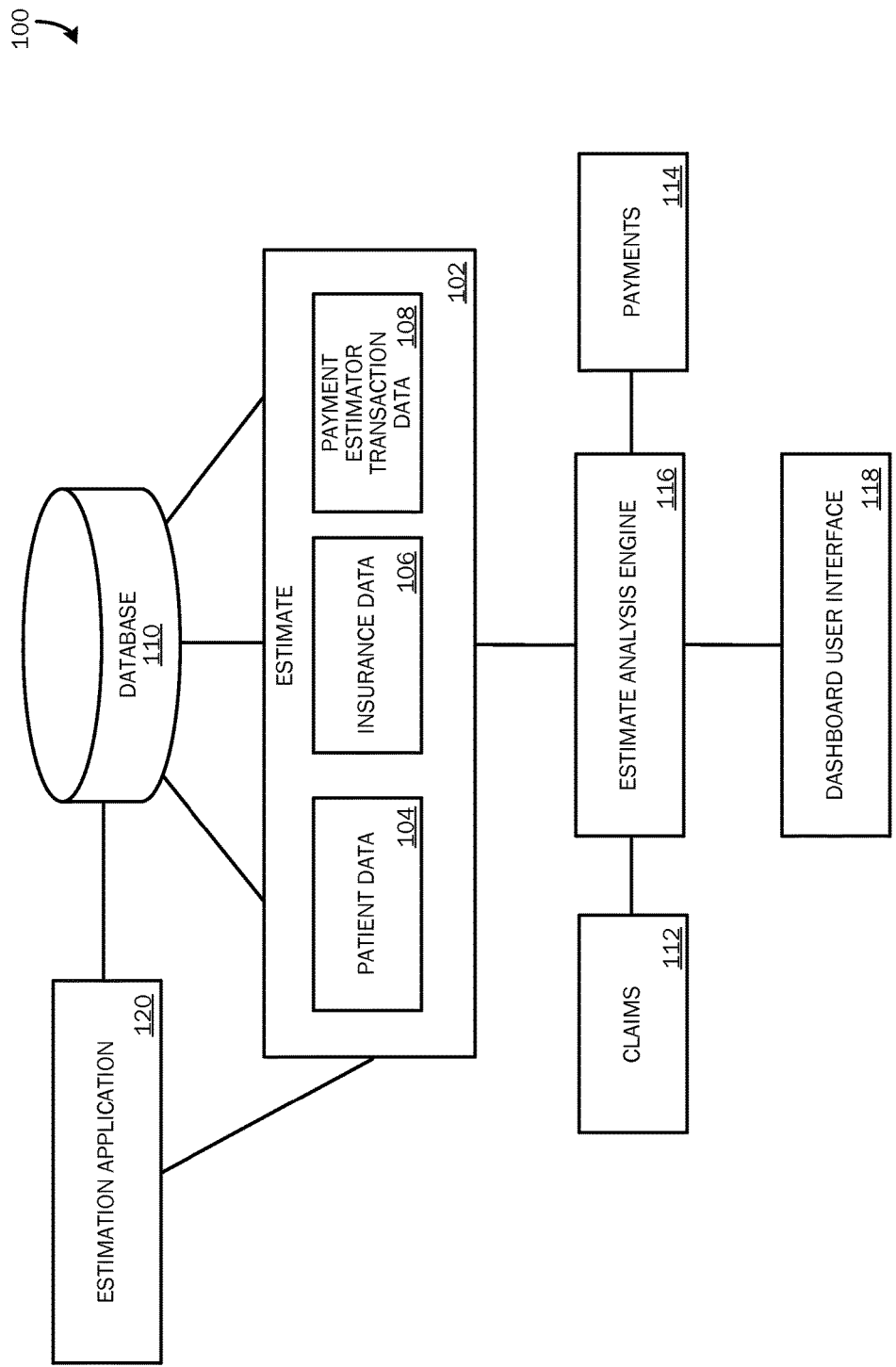
FIG. 1 is a simplified block diagram of one embodiment of a system for providing patient payment estimate validation, the system comprising an estimate analysis engine.

Embodiments provide patient payment estimate validation. Validating patient payment estimates may comprise matching patient payment estimates with claims, payments and insurance contracts and providing tools to analyze the results of the matching process. Discrepancies may be determined, for example discrepancies between procedures and patient portions from the estimate with procedures actually billed and paid and a patient portion determined by the insurance company. Results may be stored in a dashboard user interface, which may then be available via a user interface for drill-down analysis.

These embodiments may be combined, other embodiments may be utilized, and structural changes may be made without departing from the spirit or scope of the present invention. The following detailed description is therefore not to be taken in a limiting sense, and the scope of the present invention is defined by the appended claims and their equivalents. Referring now to the drawings, in which like numerals refer to like elements throughout the several figures, embodiments of the present invention and an exemplary operating environment will be described.

Referring now to FIG. 1, a simplified block diagram of one embodiment of a system 100 for providing patient payment estimate validation is illustrated. As described briefly above, when a patient seeks healthcare services from a healthcare provider, an estimate 102 may be provided to the patient or to a guarantor of the patient's account. The estimate 102 may be determined by an estimation application 120, which may incorporate various pieces of information, herein referred to as payment estimator transaction data 108, to determine the estimate 102. For example, the payment estimator transaction data 108 may include a selection of one or more procedures anticipated to be performed. A selected procedure may involve other related procedures commonly performed in conjunction with the selected procedure. For example, a colonoscopy procedure may involve anesthesia, and in some cases, a biopsy. The related procedures may be automatically provided as part of a procedure template for a selected procedure or treatment.

The estimate 102 may also incorporate other information, such as patient data 104 and insurance data 106. The patient data 104 may include a patient's name, account number, and other demographic data. The insurance data 106 may include information about if a patient has insurance coverage, and if so, who the insurance provider is, what type of plan the patient has, etc. The various pieces of information, in addition to the determined estimate may be stored in one or more databases 110.

According to embodiments, the system 100 may comprise an estimate analysis engine 116 operable to compare claims 112 and payments 114 with an estimate 102. A record may be associated with each estimate 102 completed by the estimation application 120. On a periodic basis, or when manually invoked, the estimate analysis engine 116 may parse a database 110 for records of estimates 102. According to one embodiment, the estimate analysis engine 116 may parse the database 110 for all stored estimates 102. According to another embodiment, the estimate analysis engine 116 may parse the database 110 for estimates 102 within a selected time period. According to an embodiment, an example of such an estimates analysis engine 116 is the Estimatron® software system manufactured by PASSPORT HEALTH COMMUNICATIONS INC.

The estimates 102 may be compared with claims data 112 and payments data 114. Results may be displayed in a user interface (UI), for example, a dashboard UI 118. The results may be utilized to determine an accuracy of estimates 102, and accordingly, refine and improve on the quality of the estimation system.

Figure 2:
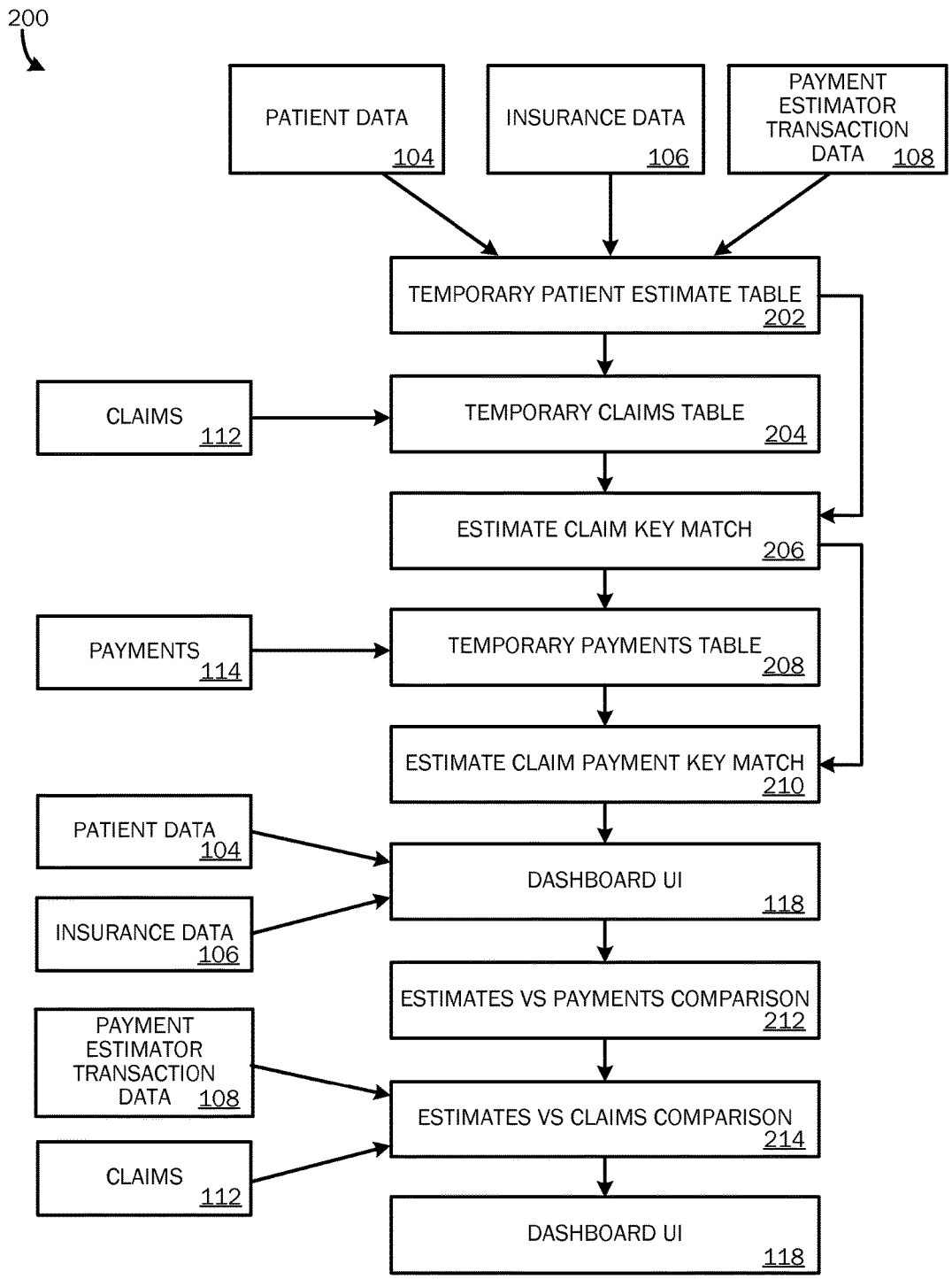
FIG. 2 illustrates a data flow for providing patient payment estimate validation.

Referring now to FIG. 2, a simplified block diagram of one embodiment of a data flow 200 for providing patient payment estimate validation is illustrated. Patient data 104, insurance data 106, and payment estimator transaction data 108 associated with an estimate 102 may be utilized to build a temporary patient estimate table 202. The temporary patient estimate table 202 may comprise account numbers found in estimates 102 that have patient identification data.

As illustrated, claims data 112 may be retrieved and utilized to build a temporary claims table 204. The data in the temporary claims table 204 may be reduced to relevant information such that information such as unique account identification numbers and patient control numbers may be obtained.

An estimate claim key match table 206 may be built from matching account numbers from the temporary patient estimate table 202 and the temporary claims table 204. Accordingly, the estimate claim key match table 206 may include a listing of pairing of estimates 102 with matching claims 112 according to account number.

As illustrated, payments data 114 may be retrieved and utilized to build a temporary payments table 204. Payments data 114 may include actual payments for a patient for a claim 112. For example, a claim 112 may be submitted to an insurance company, and the healthcare provider receives a payment from the insurance company. Payments data 114 may include payment transaction data such as unique account identification numbers or patient control numbers associated with a payment made on a claim 112.

The temporary payments table 204 may be matched with the estimate claim key match table 206, and a new table, herein referred to as an estimate claim payment key match table 210 may be built. The estimate claim payment key match table 210 may comprise a listing of account numbers and estimates 102 with patient data 104 and matching claims 112 and payments 114.

The data in the estimate claim payment key match table 210 may then be utilized to build a dashboard UI 118. An estimate dashboard detail row may be inserted for each match. Each estimate dashboard detail row may comprise key estimate data which may be selected by a user and expanded for viewing of further details.

Further reads of the patient data 104 and insurance data 106 may be performed, and additional details may be provided to the dashboard UI 118. The dashboard UI 118 may comprise a dashboard table row for every matching estimate 102, claim 112, and payment 114.

An estimates-versus-payments comparison 212 may be performed, wherein a patient responsibility amount from the estimate 102 and a patient responsibility amount from the payment 114 may be compared. For example, the patient responsibility amount calculated by the estimation application 120 may be compared with what a patient's insurance company says is the patient responsibility amount.

If the patient responsibility amount from the estimate 102 and from the payment 114 do not match, an estimates-versus-claims comparison 214 may be performed. The payment estimator transaction data 108 and the claim 112 may be analyzed, wherein a comparison between what procedures were estimated versus what procedures were billed and paid for by the patient's insurance company. The results may either be that the procedures match or they do not match. The results may be updated in the dashboard UI 118. For example, if a procedure in the estimate and in the claim matches, a procedure match count provided in the dashboard UI 118 may be incremented. If a procedure in the estimate and in the claim does not match, a procedure non-match count provided in the dashboard UI 118 may be incremented.

The dashboard UI 118 may be utilized by healthcare provider personnel or by an estimation provider. For example, the dashboard UI 118 may be utilized as a quality assurance system for periodic reviews of the accuracy of estimates 102. Output of the estimate analysis engine 116 may be utilized to build quality and reliability in the estimation application 120.

The dashboard UI 118 may be utilized to display output of the estimate analysis engine 116. A user may be able to view counts and date ranges for source data including estimates 102, claims 112, and payments 114. A count of a number of matches between estimates 102 and claims 112 may also be displayed. Additionally, a count of a number of matches between estimates 102, claims 112, and payments 114 may be provided. For matches between estimates 102, claims 112, and payments 114, a count of how many match by dollar amount may be displayed. For matches between estimates 102, claims 112, and payments 114 where the dollar amount does not match, a count of all procedures matching, no procedures matching, and some procedures matching may be displayed.

Categories may be selected, enabling a user to drill down into further detail. For example, a user may select to view source data for a row within the dashboard UI 118, and accordingly, a summary of the estimate 102 and its procedures, claim detail 112 including all charges, and payment detail 114 including any adjustments may be displayed. A user may be enabled to drill down further, and a display of how allowed charges were determined based on a contract with the patient's insurance company may be provided, which may include a summary line, a detailed audit trail showing how the procedures were priced, and the contract terms that were satisfied by the procedures in the estimate 102.

Figure 3:
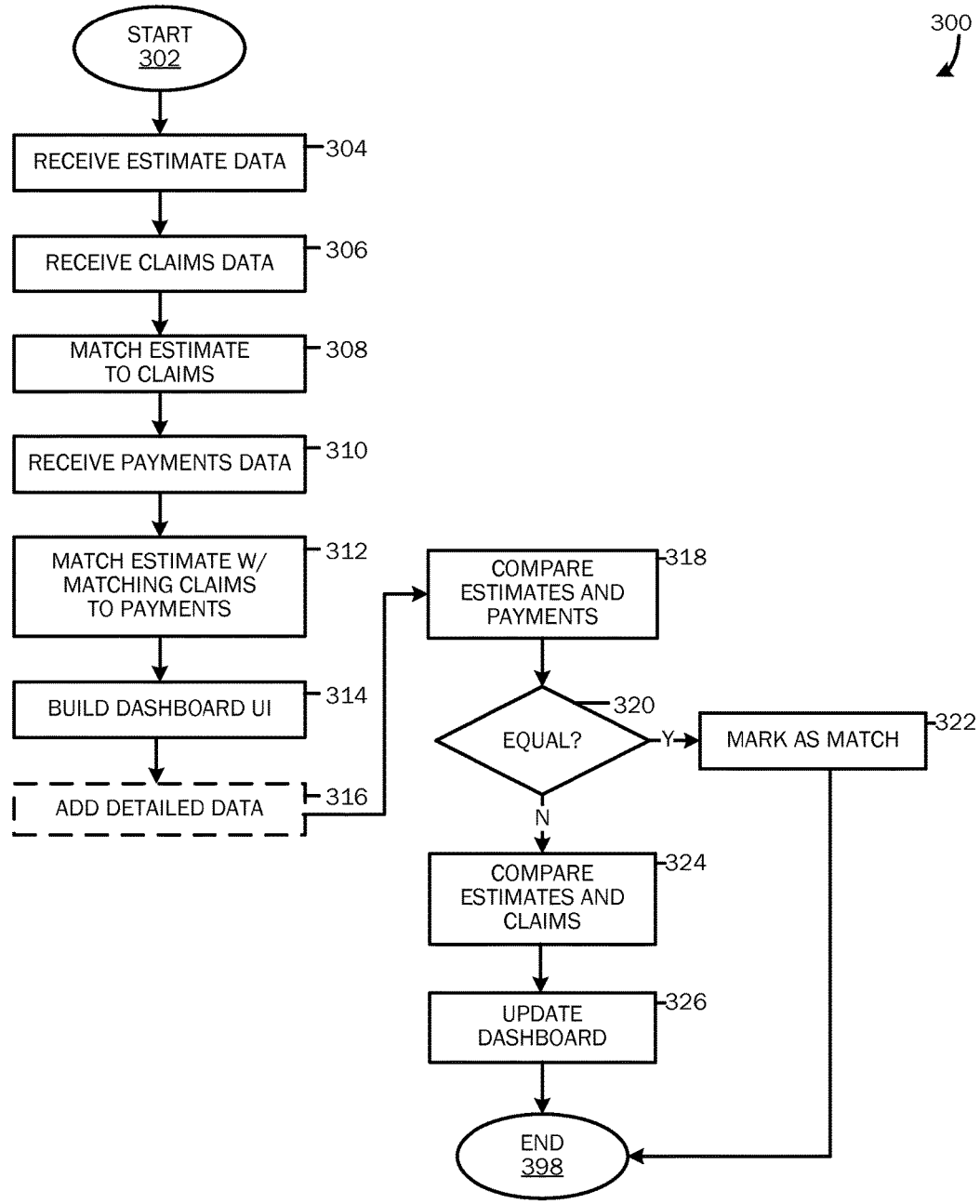
FIG. 3 illustrates a flow chart of a method for validating patient payment estimates.

Referring now to FIG. 3, a flow chart of a method 300 for validating patient payment estimates is illustrated. The method 300 starts at OPERATION 302, and proceeds to OPERATION 304, where one or more estimates 102 are received. As described above, estimates 102 may be stored in a database 110. On a periodic basis or upon receiving an indication to search for estimates 102, the estimate analysis engine 116 may parse the database 110 for estimates 102. According to one embodiment, the estimate analysis engine 116 may parse the database 110 for all stored estimates 102. According to another embodiment, the estimates analysis engine 116 may parse the database 110 for estimates 102 created within a selected time period.

Each estimate 102 may include patient data 104 (e.g., patient identification data, account numbers, etc.), insurance data 106, and payment estimator transaction data 108. A temporary patient estimate table 202 may be built from the received estimates 102, and may include account number identifications from the patient data 104 and the insurance data 106 and patient information from the payment estimator transaction data 108.

The method 300 proceeds to OPERATION 306, where claims data 112 may be received. Unique account identification numbers and patient control numbers may be extracted from the claims data 112 and stored in a temporary claims table 204. At OPERATION 308, matching account numbers from the estimates data 102 in the temporary patient estimate table 202 and from the claims data 112 in the temporary claims table 204 may be matched and stored in an estimate claim key match table 206.

The method 300 may then proceed to OPERATION 310, where payment data 114 is received. Unique account identification numbers and patient control numbers may be extracted from the payments data 114 and stored in a temporary payments table 208. At OPERATION 312, payments 114 in the temporary payments table 208 that have matching account numbers with estimates 102 and claims 112 in the estimate claim key match table 206 may be matched and stored in an estimate claim payment key match table 210.

At OPERATION 314, the dashboard UI 118 may be built. Each match in the estimate claim payment key match table 210 may be inserted into a row within the dashboard UI 118, and may comprise account numbers and estimates 102 with patient data and matching claims 112 and payments 114.

The method 300 may optionally proceed to OPERATION 316, where the estimate analysis engine 116 may retrieve additional patient data 104 and insurance data 106. As can be appreciated, the additional details may be received at OPERATION 304, or alternatively, the estimate analysis engine 116 may go back and fill in details by performing reads on the patient data 104 and insurance data 108.

The method 300 may proceed to OPERATION 318, where the estimates 102 and payments 114 may be compared. According to embodiments, the calculated patient responsibility amount as determined by the estimate analysis engine 116 and the determined patient responsibility amount as communicated from the patient's insurance company (i.e., the amount not paid by the insurance company) is compared.

At DECISION OPERATION 320, a determination may be made as to whether the patient responsibility amount in the estimate 102 is equal to the patient responsibility amount according to the payment 114. If a determination is made that the amounts are equal, the method 300 may proceed to OPERATION 322, where the estimate 102 is marked as a match. A determination may also be made as to whether the amount is a zero dollar amount.

If a determination is made that the amounts are not equal, the method 300 may proceed to OPERATION 324, where the estimate 102 is compared with the claim 112. According to embodiments, procedures included in the estimate that were anticipated to be performed, which may include a predefined template of related procedures commonly performed in conjunction with a selected procedure, may be compared with procedures that were billed to the patient's insurance company. If a procedure matches, it may be marked as a procedure match. If a procedure does not match, it may be marked as a non-matching procedure. If an estimate 102 and/or claim 112 includes a plurality of procedures, some procedures may match and some may not.

The method 300 may proceed to OPERATION 326, where the dashboard UI 118 may be updated with counts of matches between estimates 102 and claims 112, counts of matches between estimates 102, claims 112, and payments 114, and for three-way matches (i.e., estimates, claims, and payments), a count of how many matched on dollar amount. The dashboard UI 118 may also include a count of all procedures matching, a count of procedures that do not match, and a count of where some procedures match. As described above, the dashboard UI 118 may include selectable categories, lines, and items such that a user may be enabled to select a category, line, or item and see details associated with the estimate 102, claim 112, and/or payment 114.

Embodiments may be utilized to refine and improve on the quality of an estimation system (i.e., estimation application 120). For example, results may be analyzed to determine if inaccuracies may be a result of a mismatch between the procedure or procedures utilized to calculate an estimate 102 and the actual procedures performed and billed. Embodiments may also be utilized to determine if inaccuracies may be a result of a mismatch even though the procedures are the same. Embodiments may also be utilized to refine a template of related procedures by providing information that may be utilized to determine procedures that may be commonly bundled. Additionally, embodiments may be utilized to determine discrepancies between an estimate 102 and an amount billed.

Additionally, embodiments may be utilized for other types of quality assurance. The information may be utilized to find discrepancies between what an insurance company is paying and what a healthcare provider determines the insurance company should be paying. For example, a healthcare provider may determine that they may not be paid properly by an insurance company. The method 300 ends at OPERATION 398.

As described above, embodiments of the invention may be implemented via local and remote computing and data storage systems. Such memory storage and processing units may be implemented in a computing device, such as computing device 400 of FIG. 4. Any suitable combination of hardware, software, or firmware may be used to implement the memory storage and processing unit. For example, the memory storage and processing unit may be implemented with computing device 400 or any other computing devices 418, in combination with computing device 400, wherein functionality may be brought together over a network in a distributed computing environment, for example, an intranet or the Internet, to perform the functions as described herein. Such systems, devices, and processors (as described herein) are examples and other systems, devices, and processors may comprise the aforementioned memory storage and processing unit, consistent with embodiments of the invention.

Figure 4:
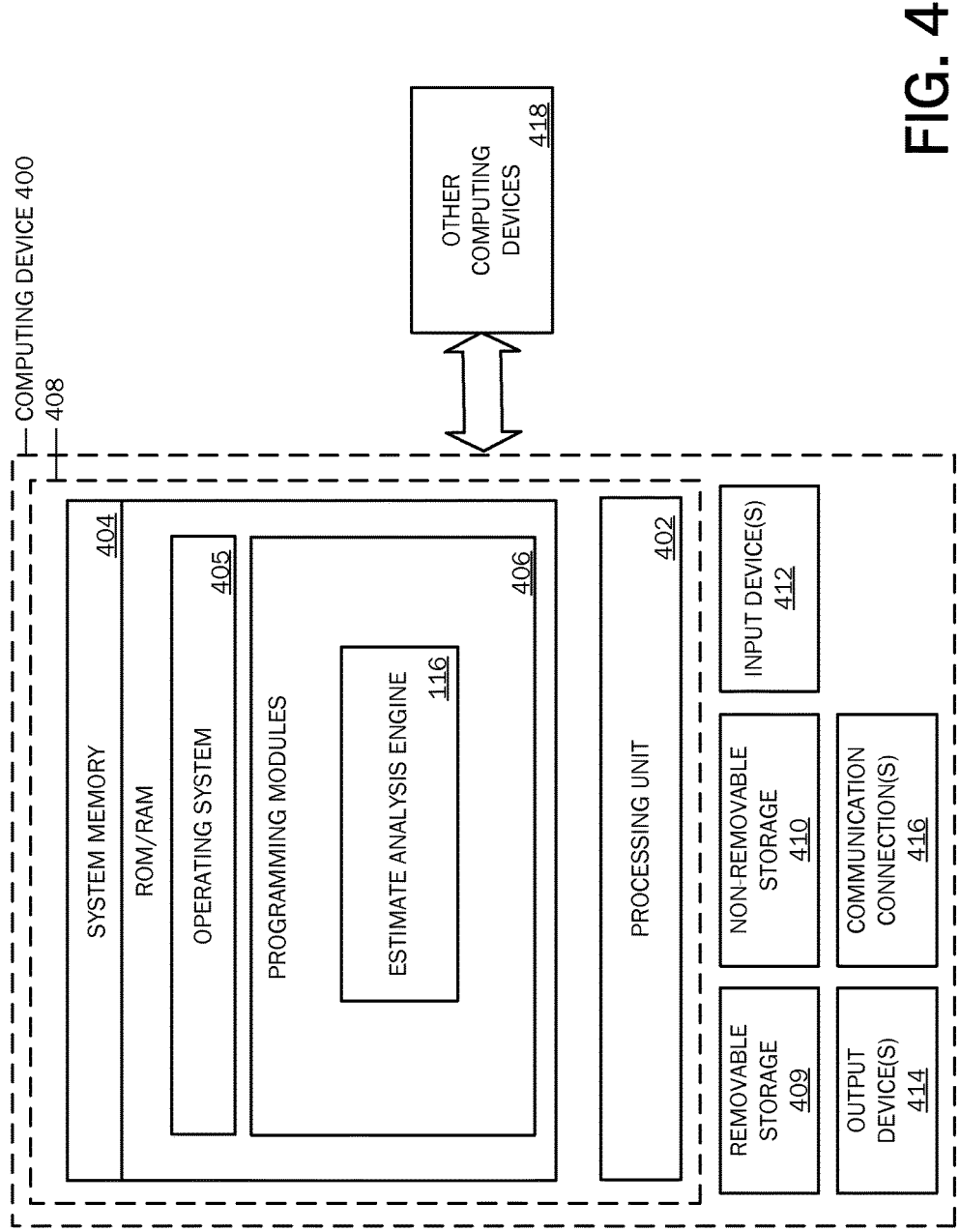
FIG. 4 is a simplified block diagram of a computing device with which embodiments of the present invention may be practiced.

With reference to FIG. 4, a system consistent with embodiments of the invention may include one or more computing devices, such as computing device 400. The computing device 400 may include at least one processing unit 402 and a system memory 404. The system memory 404 may comprise, but is not limited to, volatile (e.g. random access memory (RAM)), non-volatile (e.g. read-only memory (ROM)), flash memory, or any combination. System memory 404 may include operating system 405, one or more programming modules 406, and may include an estimate analysis engine 116, wherein the information standardization and verification application is a software application having sufficient computer-executable instructions, which when executed, performs functionalities as described herein. Operating system 405, for example, may be suitable for controlling computing device 400's operation. Furthermore, embodiments of the invention may be practiced in conjunction with a graphics library, other operating systems, or any other application program and is not limited to any particular application or system. This basic configuration is illustrated in FIG. 4 by those components within a dashed line 408.

Although embodiments of the present invention have been described as being associated with data stored in memory and other storage mediums, data can also be stored on or read from other types of computer-readable media, such as secondary storage devices, like hard disks, floppy disks, or a CD-ROM, or other forms of RAM or ROM. Further, the disclosed methods' stages may be modified in any manner, including by reordering stages and/or inserting or deleting stages, without departing from the invention.

The computing device 400 may also include additional data storage devices (removable and/or non-removable) such as, for example, magnetic disks, optical disks, or tape. Such additional storage is illustrated in FIG. 4 by a removable storage 409 and a non-removable storage 410. Computing device 400 may also contain a communication connection 416 that may allow device 400 to communicate with other computing devices 418, such as over a network in a distributed computing environment, for example, an intranet or the Internet. Communication connection 416 is one example of communication media.

Program modules, such as the estimate analysis engine 116, may include routines, programs, components, data structures, and other types of structures that may perform particular tasks or that may implement particular abstract data types. Moreover, embodiments of the invention may be practiced with other computer system configurations, including hand-held devices, multiprocessor systems, microprocessor-based or programmable user electronics, minicomputers, mainframe computers, and the like. Embodiments of the invention may also be practiced in distributed computing environments where tasks are performed by remote processing devices that are linked through a communications network. In a distributed computing environment, program modules may be located in both local and remote memory storage devices.

Furthermore, embodiments of the invention may be practiced in an electrical circuit comprising discrete electronic elements, packaged or integrated electronic chips containing logic gates, a circuit utilizing a microprocessor, or on a single chip containing electronic elements or microprocessors. Embodiments of the invention may also be practiced using other technologies capable of performing logical operations such as, for example, AND, OR, and NOT, including but not limited to mechanical, optical, fluidic, and quantum technologies. In addition, embodiments of the invention may be practiced within a general purpose computer or in any other circuits or systems.

Embodiments of the invention, for example, may be implemented as a computer process (method), a computing system, or as an article of manufacture, such as a computer program product or computer readable media. The computer program product may be a computer storage media readable by a computer system and encoding a computer program of instructions for executing a computer process. Accordingly, the present invention may be embodied in hardware and/or in software (including firmware, resident software, microcode, etc.). In other words, embodiments of the present invention may take the form of a computer program product on a computer-usable or computer-readable storage medium having computer-usable or computer-readable program code embodied in the medium for use by or in connection with an instruction execution system. A computer-usable or computer-readable medium may be any medium that can contain, store, communicate, propagate, or transport the program for use by or in connection with the instruction execution system, apparatus, or device.

Embodiments of the present invention, for example, are described above with reference to block diagrams and/or operational illustrations of methods, systems, and computer program products according to embodiments of the invention. For example, FIGS. 1-4 and the described functions taking place with respect to each illustration may be considered steps in a process routine performed by one or more local or distributed computing systems. The functions/acts noted in the blocks may occur out of the order as shown in any flowchart. For example, two blocks shown in succession may in fact be executed substantially concurrently or the blocks may sometimes be executed in the reverse order, depending upon the functionality/acts involved.

While the specification includes examples, the invention's scope is indicated by the following claims. Furthermore, while the specification has been described in language specific to structural features and/or methodological acts, the claims are not limited to the features or acts described above. Rather, the specific features and acts described above are disclosed as example for embodiments of the invention.

It will be apparent to those skilled in the art that various modifications or variations may be made in the present invention without departing from the scope or spirit of the invention. Other embodiments of the invention will be apparent to those skilled in the art from consideration of the specification and practice of the invention disclosed herein.

All rights including copyrights in the code included herein are vested in and the property of the Applicant. The Applicant retains and reserves all rights in the code included herein, and grants permission to reproduce the material only in connection with reproduction of the granted patent and for no other purpose.

I claim:

1. A computer-implemented method of using one or more computer hardware components including a computer processor to generate a dashboard user interface (UI) according to an estimate claim payment key match table comprising:

using an estimation application to determine one or more estimates associated with one or more services according to one or more procedures anticipated to be performed for the one or more services including a template of related procedures commonly performed in conjunction with the one or more procedures;

storing the one or more estimates associated with one or more services as records in a database;

using an estimate analysis engine to parse the records of the database, wherein output of the estimate analysis engine is utilized to build quality and reliability in the estimation application by determining if inaccuracies are a result of a mismatch between the one or more procedures utilized to calculate the one or more estimates and actual procedures performed and billed;

building a temporary patient estimate table structured with patient data, insurance data, and estimate data for the one or more estimates associated with the one or more services, wherein the patient data includes a patient name, an account number, and other demographic data;

building a temporary claims table structured with claims data for one or more claims associated with the one or more services;

building an estimate claim key match table structured by matching one or more account numbers in the temporary patient estimate table with one or more account numbers in the temporary claims table including pairing the one or more estimates with one or more matching claims according to the one or more matching account numbers;

building a temporary payments table structured with payments data for one or more payments associated with the one or more services;

building the estimate claim payment key match table structured by matching the temporary payments table with the estimate claim key match table to include a listing of account numbers and estimates with patient data and matching claims and payments;

building and displaying the dashboard UI structured with data output from the estimate analysis engine that includes data from the estimate claim payment key match table, wherein the building includes inserting an estimate dashboard detail row into the dashboard UI that includes account numbers and estimates with patient data and matching claims and payments;

updating the dashboard UI by incrementing an estimate and payment match count provided in the dashboard UI for equal estimates and payments;

updating the dashboard UI by incrementing a procedure match count provided in the dashboard UI for matching procedures and estimates;

updating the dashboard UI by incrementing a procedure non-match count provided in the dashboard UI for non-matching procedures and estimates, wherein the dashboard UI provides a quality assurance system for review of accuracy of the one or more procedures and the one or more estimates; and refining the template of related procedures by determining particular procedures to bundle together to build quality and reliability in the estimation application.

2. The method of claim 1, further comprising comparing unequal estimates and claims having matching account numbers and determining whether one or more procedures in the one or more estimates and one or more procedures in the one or more claims match.

3. The method of claim 2, further comprising displaying, via the dashboard UI, a detailed audit trail showing pricing of the one or more procedures, and contract terms satisfied by the one or more procedures associated with the one or more estimates.

4. The method of claim 2, further comprising determining whether a procedure and any related procedures in each estimate match procedures billed to and paid by a patient's insurance company.

5. The method of claim 1, further comprising building the temporary patient estimate table after receiving the estimate data.

6. The method of claim 5, further comprising building the temporary claims table after receiving the claims data.

7. The method of claim 1, further comprising building the temporary payments table after receiving the payments data.

8. The method of claim 7, further comprising-displaying one or more counts and one or more date ranges for source data from estimates, claims, and payments in the dashboard UI including a count of a number of matches between estimates, claims, and payments.

9. The method of claim 1, further comprising updating the dashboard UI by incrementing match counts for matching or non-matching procedures.

10. The method of claim 1, further comprising determining whether a patient responsibility amount calculated in each estimate matches a patient responsibility amount calculated by a patient's insurance company.

11. A system to generate a dashboard user interface (UI) according to an estimate claim payment key match table comprising:

a memory storage; and one or more processors coupled to the memory storage, wherein the one or more processors are operable to:

use an estimation application to determine one or more estimates associated with one or more services according to one or more procedures anticipated to be performed for the one or more services that includes a template of related procedures commonly performed in conjunction with the one or more procedures;

store the one or more estimates associated with one or more services as records in a database;

use an estimate analysis engine to parse the records of the database, wherein output of the estimate analysis engine is utilized to build quality and reliability in the estimation application;

build a temporary patient estimate table structured with patient data, insurance data, and estimate data for the one or more estimates associated with the one or more services, wherein the patient data includes a patient name, an account number, and other demographic data;

build a temporary claims table structured with claims data for one or more claims associated with the one or more services;

build an estimate claim key match table structured by matching one or more account numbers in the temporary patient estimate table and one or more account numbers in the temporary claims table including pairing the one or more estimates with one or more matching claims according to the one or more matching account numbers;

build a temporary payments table structured with payments data for one or more payments associated with the one or more services;

build the estimate claim payment key match table structured by matching the temporary payments table with the estimate claim key match table to include a listing of account numbers and estimates with patient data and matching claims and payments;

build and display the dashboard UI structured with data output from the estimate analysis engine that includes data from the estimate claim payment key match table, wherein to build includes insertion of an estimate dashboard detail row into the dashboard UI that includes account numbers and estimates with patient data and matching claims and payments;

update the dashboard UI by incrementing an estimate and payment match count provided in the dashboard UI for equal estimates and payments, wherein the dashboard UI provides a quality assurance system for review of accuracy of the one or more estimates;

update the dashboard UI by incrementing a procedure match count provided in the dashboard UI for matching procedures and estimates;

update the dashboard UI by incrementing a procedure non-match count provided in the dashboard UI for non-matching procedures and estimates, wherein the dashboard UI provides a quality assurance system for review of accuracy of the one or more procedures and the one or more estimates; and refine the template of related procedures by determining particular procedures to bundle together to build quality and reliability in the estimation application.

12. The system of claim 11, wherein the one or more processors are further operable to:

compare unequal estimates and claims having matching account numbers and determine whether one or more procedures in the one or more estimates and one or more procedures in the one or more claims match.

13. The system of claim 12, wherein the one or more processors are further operable to determine whether a procedure and any related procedures in each estimate match procedures billed to and paid by a patient's insurance company.

14. The system of claim 11, wherein the one or more processors are further operable to determine whether a patient responsibility amount calculated in each estimate matches a patient responsibility amount calculated by a patient's insurance company.

15. A non-transitory computer readable medium containing computer executable instructions, which when executed, perform a method of using one or more computer hardware components including a computer processor to generate a dashboard user interface (UI) according to an estimate claim payment key match table comprising:

using an estimation application to determine one or more estimates associated with one or more services according to one or more procedures anticipated to be performed for the one or more services including a template of related procedures commonly performed in conjunction with the one or more procedures;

storing the one or more estimates associated with one or more services as records in a database;

using an estimate analysis engine to parse the records of the database, wherein output of the estimate analysis engine is utilized to build quality and reliability in the estimation application;

building a temporary patient estimate table structured with patient data, insurance data, and estimate data for the one or more estimates associated with the one or more services, wherein the patient data includes a patient name, an account number, and other demographic data;

building a temporary claims table structured with claims data for one or more claims associated with the one or more services;

building an estimate claim key match table structured by matching one or more account numbers in the temporary patient estimate table and one or more account numbers in the temporary claims table including pairing the one or more estimates with one or more matching claims according to the one or more matching account numbers;

building a temporary payments table structured with payments data for one or more payments associated with the one or more services;

building the estimate claim payment key match table structured by matching the temporary payments table with the estimate claim key match table to include a listing of account numbers and estimates with patient data and matching claims and payments;

building and displaying the dashboard UI structured with data output from the estimate analysis engine that includes data from the estimate claim payment key match table, wherein the building includes inserting an estimate dashboard detail row into the dashboard UI that includes account numbers and estimates with patient data and matching claims and payments;

updating the dashboard UI by incrementing an estimate and payment match count provided in the dashboard UI for equal estimates and payments, wherein the dashboard UI provides a quality assurance system for review of accuracy of the one or more estimates;

updating the dashboard UI by incrementing a procedure match count provided in the dashboard UI for matching procedures and estimates;

updating the dashboard UI by incrementing a procedure non-match count provided in the dashboard UI for non-matching procedures and estimates, wherein the dashboard UI provides a quality assurance system for review of accuracy of the one or more procedures and the one or more estimates; and refining the template of related procedures by determining particular procedures to bundle together to build quality and reliability in the estimation application.

16. The computer readable medium of claim 15, further comprising comparing unequal estimates and claims having matching account numbers and determining whether one or more procedures in the one or more estimates and one or more procedures in the one or more claims match.

17. The computer readable medium of claim 16, further comprising determining whether a procedure and any related procedures in each estimate match procedures billed to and paid by a patient's insurance company.

18. The computer readable medium of claim 15, further comprising determining whether a patient responsibility amount calculated in each estimate matches a patient responsibility amount calculated by a patient's insurance company.

* * * * *